(12) United States Patent
Seaman

(10) Patent No.: US 6,482,388 B1
(45) Date of Patent: Nov. 19, 2002

(54) COMBINED BODY LENGTH IN THE SELECTIVE BREEDING OF THOROUGHBRED RACEHORSES

(76) Inventor: Cecil O. Seaman, P.O. Box 11370, Lexington, KY (US) 40575

( * ) Notice: Subject to any disclaimer, the term of this patent is extended or adjusted under 35 U.S.C. 154(b) by 0 days.

(21) Appl. No.: 09/149,388

(22) Filed: Sep. 8, 1998

(51) Int. Cl.[7] .............................................. A61K 49/00
(52) U.S. Cl. ...................................................... 424/9.1
(58) Field of Search .............................. 800/8; 424/9.1, 424/9.2

(56) References Cited

PUBLICATIONS

Hodgson, D. et al. The Athletic Horse. Philadelphia: W.B. Saunders Company. 1994, pp. 20, 21, 24, 25, and 42–45.*
Kobluk, C. et al. 'The Effect of Conformation and Shoeing: A Cohort Study of 95 Thoroughbred Racehorses.' In Proceedings of the Thirty–fifth Annual Convention of the American Association of Equine Practitioners. Edited by M. Royer. Lexington, Kentucky, 1990.*
Koenen, E.P.C. et al. Genetic Parameters of Linear Scored Conformation Traits and their Relation to Dressage and Show–Jumping Performance in the Dutch Warmblood Riding Horse Population. Livestock Production Science. 43:85–94, 1995.*
Green, B. Horse Conformation as to Soundness and Performance. Northland Press, 1975, pp. 10–18, 22–25, 58–61.*
Haun, M. The X Factor: What It is & How to Find It. Neenah, Wisconsin: The Russell Meerdink Company, Ltd., 1997, pp. 27–31, 33–42, 57–63, 133–135, 137, 167–168.*
Nicking Patterns Database (http://nicking.com), NPD Software, 1997.*
C Seaman et al., website:www.cecilseaman.com.*
Henry Q. Murphy, "Fit v. Fat," Thoroughbred Times, p. 16–17, (Jul. 9, 1993).

* cited by examiner

*Primary Examiner*—Deborah Crouch
*Assistant Examiner*—Joseph Woitach
(74) *Attorney, Agent, or Firm*—Eugene Chovanes

(57) ABSTRACT

To increase the chances of breeding an elite racehorse, a genetic dominance tree (GDT) of the prospective dam, and a GDT of the prospective sire, are constructed. A GDT has indicia for determining whether the horse has any dominant and substantially constant representative physical characteristic in the form of a combined body length (CBL) in its family. The prospective sire and dam are bred where there is such a dominant and relatively constant CBL common to both horses.

24 Claims, 4 Drawing Sheets

(3 of 4 Drawing Sheet(s) Filed in Color)

COMBINED BODY LENGTH IN THE SELECTIVE BREEDING OF THOROUGHBRED RACEHORSES

BACKGROUND OF THE INVENTION

1. Field of the Invention

The invention relates to the selective breeding of thoroughbred racehorses to achieve an elite racehorse having racing class and capable of optimum speed and soundness. Such selective breeding concentrates the same or similar physical traits from the family tree of the sire and dam to create a homogeneous family.

2. Prior Art

A thoroughbred horse is a specific breed of horse. Thoroughbred horse races use such breed of horse.

The thoroughbred racehorses, which run in such races, are the result of controlled breeding that has occurred over hundreds of years. Records are meticulously maintained and rigidly controlled with respect to the sire and dam of all thoroughbred racehorses. The racing records, which give the times and performance of a given racehorse in each of its races, are again carefully maintained. Generally speaking, the faster a racehorse can run, under given distances and conditions, the more desirable and valuable is the racehorse.

Racehorses, which create stellar racing records, are considered elite racehorses. Such elite racehorses are rare. Out of the about 50,000 thoroughbred foals born each year, very few become top flight racehorses, and even fewer become elite racehorses, such as stakes winners. Some 3% of the racehorses born each year become stakes winners.

It is, of course, commonly known and accepted that a substantial factor in creating an elite racehorse, is its breeding. It is known that certain sires have had many fast and successful, and hence valuable, progeny. Northern Dancer, for instance, has had more elite racehorses in his progeny by far than most other sires. He had an outstanding racing record and has been able to pass these characteristics of speed to his progeny, and to succeeding generations.

On the other hand, other outstanding male racehorses, such as Secretariat, were far less successful as sires and could not pass on their outstanding racing ability to any great extent.

In both examples set forth above, the prior art practice of selection of racehorses for breeding was followed. Simply put, a fast sire was bred to a fast mare based on the individual racing record of both the sire and mare. It was also observed that certain families or blood lines consistently produced good racehorses when combined with other families or blood lines. However, such breeding selections were hit or miss and inconsistent, and therefore unreliable.

SUMMARY OF THE PRESENT INVENTION

The objective of the present invention is to provide means for aiding in the breeding of racehorses having the elite racehorse as its standard. In order to achieve such breeding on a more successful basis than in the past, the invention provides a genetic analysis, by means of a genetic dominance tree (GDT) constructed for the given racehorse being considered for breeding. To create such a GDT, the invention first requires that a representative physical characteristic be established, which is measurable in each racehorse. I have determined that a specific length measurement on the racehorse is a desirable representative physical characteristic. This specific measurement is of a combined body length (CBL) of a racehorse.

Based on enough actual measurements of such CBL's, the range of the measurements of this characteristic is then charted, in increments, for a representative thoroughbred racehorse population. The resulting chart is representative of the entire thoroughbred racehorse population. The representative physical characteristic (CBL) is then analyzed in the GDT using indicia to indicate its incremental position in the thoroughbred racehorse population, to see whether there is a dominant constant of such (CBL) characteristic in the GDT of a given racehorse.

Matings are made between a given sire and mare when the dominant constant representative physical characteristic (CBL) in the GDT of the sire and mare are compatible. I have determined that in such a mating, the progeny have improved chances of inheriting this same dominant representative physical characteristics which in turn yields a horse having desirable conformation consistent with its heredity. Such consistency increases its chances of being an elite racehorse.

In summary, the present invention is directed to genetic analysis means in the form of a GDT having means for determining whether, over successive generations in the family tree of a horse, (1) there exists a dominant representative physical characteristic (CBL), and if it does exist, (2) the identity of such dominant constant representative physical characteristic. A mating is made between a sire and dam wherein each has a dominant constant that is compatible with the other.

DESCRIPTION OF THE DRAWINGS

The file of this patent contains at least one drawing executed in color. Copies of this patent with color drawings will be provided by the Patent and Trademark Office upon request and payment of the necessary fee.

FIGS. 1 and 2 illustrate the dimensions A and B that are added to get a combined body length (CBL) measurement of a horse.

DETAILED DESCRIPTION OF THE INVENTION

I have discovered that the chances of breeding an elite horse are remarkably improved when (a) the mated sire and mare are very similar in size, structure, and body type, and possess the same physical characteristics and biomechanics, and (b) that those similarities are dominant and substantially constant ("dominant constant") in the family tree history of the respective mates.

The present invention is directed to genetic analysis means for analyzing the family tree of a horse over successive generations whereby (1) it can be readily determined whether such dominant constant exists, and (2) if it does exist, identified.

I call such means a "genetic dominance tree" or "GDT".

The GDT uses a representative physical characteristic of the racehorse, which is measurable in each racehorse. The representative physical characteristic used herein is the combined body length (CBL) of the racehorse. I have found that the CBL is related to the biomechanics of a racehorse. The biomechanics of a racehorse depends on its size, structure, and body type. Such CBL is determined by measuring two specific distances within points on the racehorse while the racehorse is at rest. These distances are then added to determine the combined body length (CBL) of the racehorse. It is necessary of course for these measurements to be obtained over successive generations, so the subject matter of the invention requires substantial efforts to obtain such length measurements.

The invention requires first a construction of a profile of the CBL's of the racehorse population, based on a representative group of horses that have been measured. The CBL's are incrementally represented in the profile, which can be, for instance, in chart form.

Second, a GDT is constructed of the CBL's of each of the prospective mates, the sire and the mare, using indicia or designations, such as color, based on the increment in which the CBL fell in the representative racehorse population profile.

Third, the GDT is then examined to see whether there is a dominant constant CBL within each genetic family tree. If such dominant constant CBL does occur in the horse and its previous generations, the prospect of breeding such horse successfully to obtain an elite racehorse progeny is substantially enhanced providing such breeding is to a mate which likewise has that dominant constant CBL.

Such means for determining whether such dominant constant CBL prevails in previous generations can be, as indicated, in color chart form, as well as any other form that can readily indicate what dominant constant exists, if any, in a GDT, including computer readouts.

The combined body length (CBL) measurement consists of two straight line measurements. Both measurements are taken of the racehorse in a relaxed, standing position.

Figure 1:
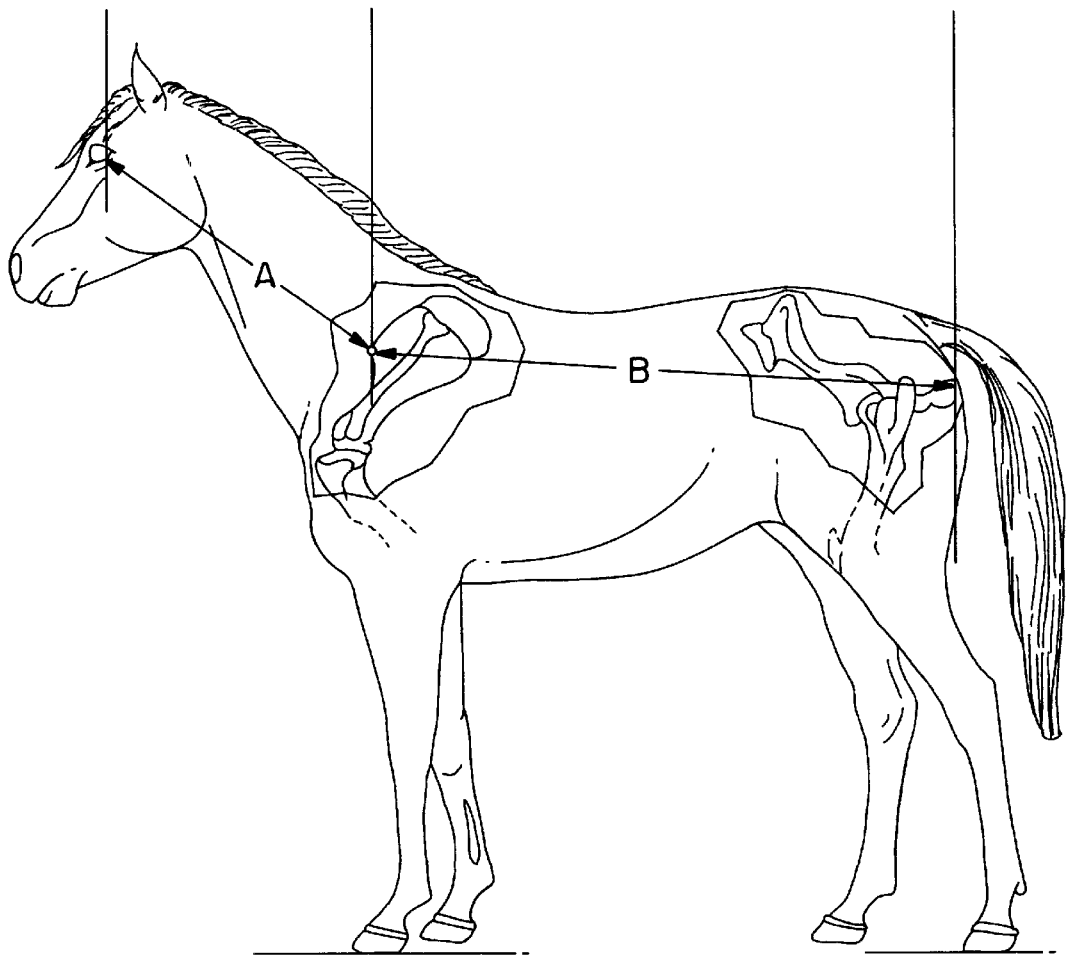
FIG. 1 is a right side elevational view of a horse at rest with broken away portions.

One of the measurements A is a straight line measurement from the lateral canthus (rear corner) of the horse's eye to a middle point on the front of the scapula. This point is shown clearly in FIG. 1 and can be described as the forwardmost point on the upper body portion of the scapula. The second measurement B is the same point in the racehorse's scapula to the hind point on the skin over the racehorse's ischium. The ischium can be readily determined by feel, since it is the most hind point of the racehorse's skeleton right under the racehorse's tail.

Both the measurements are combined to yield the racehorse's combined body length (CBL).

Figure 2:
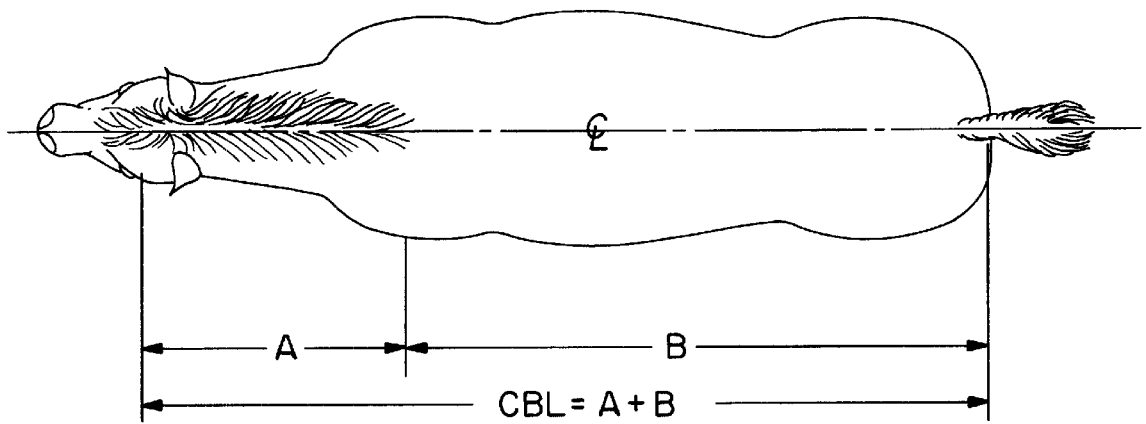
FIG. 2 is a top plan view of the horse of FIG. 1.

Both measurements are also taken in the same vertical plane, as seen in FIG. 2, which may be any plane that extends parallel to the vertical plane which runs longitudinal through the mid-section of the racehorse.

Figure 3:
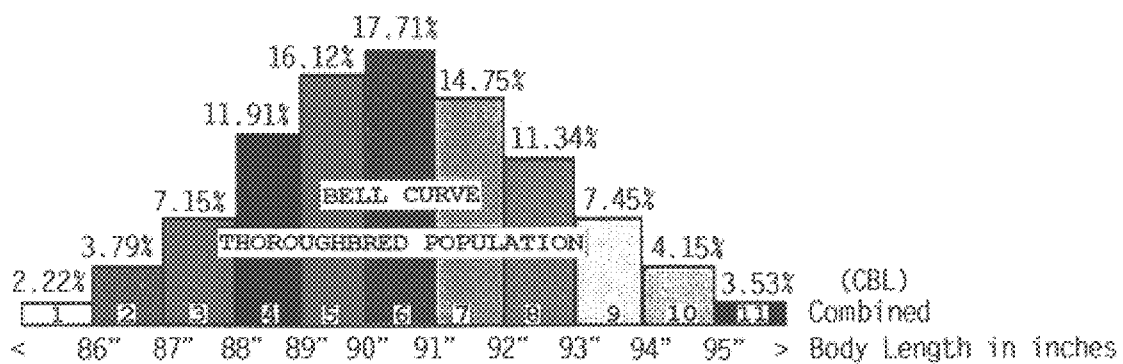
FIG. 3 is a bell curve in color of the CBL's of a representative thoroughbred racehorse population showing a range of CBLs from 85 to 96 inches.

Based on a representative number of CBL's of individual racehorses, I have determined that, plotted in bar graph form, one inch increments of CBL's would constitute a bell-like curve, as seen in FIG. 3. It shows that the range of CBL's in the general racehorse population ranges between 85 inches and 96 inches, with the largest number of racehorses in the increment between 90 inches and 91 inches and tapering off on both the higher and lower increments.

Indicia are assigned to each of the increments of measurement of CBL in such curve. For instance, the indicia could be a different color for each bar increment, or a different number, as seen in FIG. 3. Each color or number represents a different one inch increment of CBL.

A genetic dominance tree (GDT) of the horse is then constructed to indicate what, if any, dominant constant CBL exists.

To illustrate the actual construction of a GDT, reference will be made to FIG. 4 which is a chart of a genetic dominance tree (GDT) of an actual sire, Red Ransom.

Figure 4:
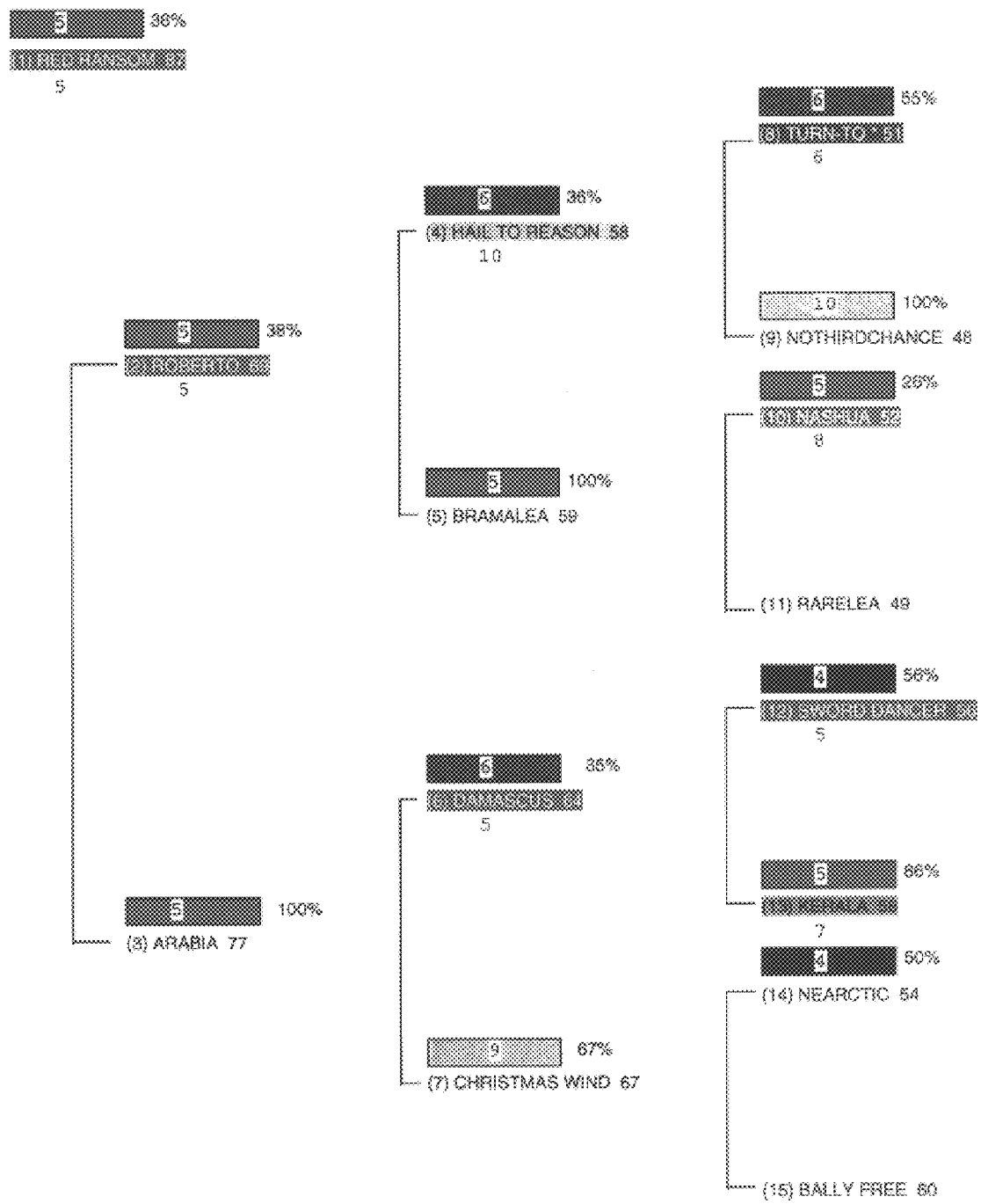
FIG. 4 is a genetic dominance tree (GDT) in color of a thoroughbred sire, Red Ransom.

The GDT of Red Ransom is set forth in FIG. 4 in conventional diagram form. The name of the racehorse is set forth within the block, where the actual CBL of the racehorse is known. The block is colored and keyed to the Bell curve of FIG. 3 to indicate the CBL. The number in parenthesis before the horse's name is the successive number of the horse considered in the tree. The racehorse's year of birth is set forth behind the racehorse's name. The colored box above the racehorse's name indicates the dominant CBL of its progeny, again color keyed to the representative Bell curve of FIG. 3. The percentage number behind the colored box above the racehorses name indicates the percentage of the racehorses progeny that had a CBL as represented by that color.

The GDT of Red Ransom shown in FIG. 4 in the block around his name indicates that his CBL is in increment 5 of the Bell curve of FIG. 3 which in turn has been designated with the color red. The number behind his name indicates he was born in 1987. The block above his name indicates the dominant CBL in his progeny is category 5, red, the same as Red Ransom, and that 38% of his progeny were in this category of CBL.

Continuing with the GDT in FIG. 4, it can be seen that the sire of Red Ransom, Roberto, is also a 5 in the Bell curve.

The dam of Red Ransom, Arabia, whose CBL is unknown, had 100% of her progeny in category 5, red.

A further analysis of the GDT of Red Ransom as seen in FIG. 4, clearly shows a consistent, dominant, CBL in the tree. The dominant CBL in Red Ransom's GDT is category 5 in the representative Bell Curve of FIG. 3, indicated in red. Such CBL is between 89" and 90".

In determining a proposed mating with Red Ransom, a GDT would be constructed for a proposed dam. Should the dominant constant CBL in the proposed dam's family be identified in red, category 5, the prospects for a successful offspring from a mating of Red Ransom and the mare would be enhanced, with the likelihood that the progeny would inherit the speed and racing class of its ancestors.

In the event the proposed dam has no dominant constant, or the dominant constant is other than red, category 5, a mating with Red Ransom would be discouraged.

As seen above with reference to FIG. 4, Red Ransom has a strong, homogeneous family tree showing a lot of the same color, which indicates dominance of a CBL of between 89" and 90". This dominant CBL indicates the family of Red Ransom possesses the ability to reproduce their own dominant characteristics in their offspring.

Figure 5:
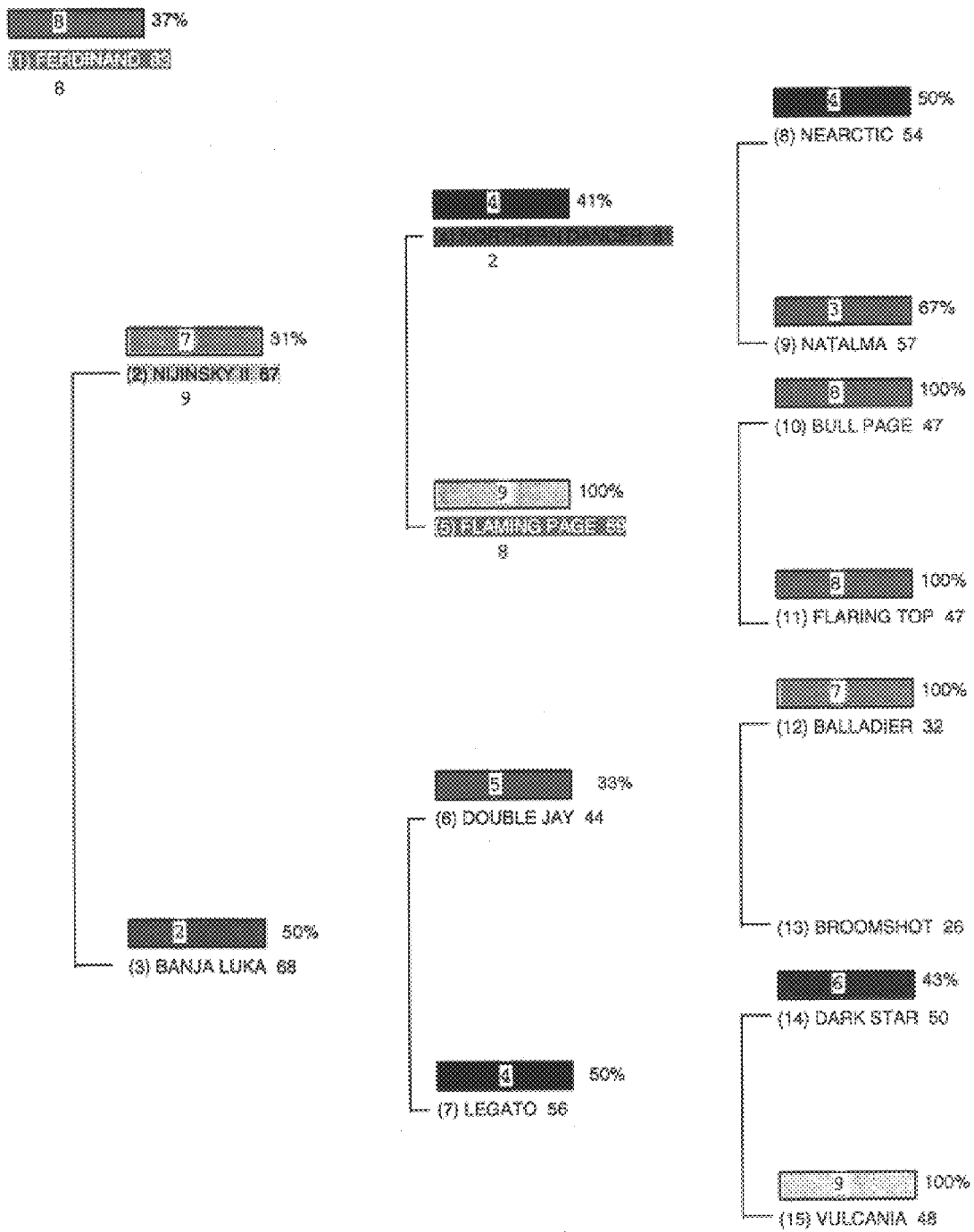
FIG. 5 is a genetic dominance tree (GDT) in color of a thoroughbred sire, Ferdinand.

There is shown in FIG. 5, the GDT of the sire Ferdinand. It is clear from an analysis of this tree, in view of the above explained procedure, that there is no dominant CBL. The progeny of Ferdinand himself are predominantly between 92" and 93". Virtually all its ancestors have different category CBL's, with no dominance. Ferdinand, in accordance with the teaching of the present invention, is a poor prospect for breeding to achieve an elite racehorse. The family of Ferdinand possesses no dominant CBL whereby the racehorse Ferdinand can be selectively bred with a matching dominant CBL. Thus, there is little likelihood that the progeny of Ferdinand would possess the speed and racing class of an elite racehorse.

The racing records of Red Ransom's and Ferdinand's progeny, respectively, bear out the above analysis. Whereas Red Ransom has been able to pass on his family's desirable biomechanics to produce elite racehorses, Ferdinand progeny have been relatively unsuccessful as racehorses.

I claim:

1. In a system of selecting a sire and a dam for breeding a racehorse, having:
   a. means for determining a measurement of a representative physical characteristic in the form of a combined body length (CBL) on each of a sufficient number of thoroughbred racehorses to yield a representative profile of the measurements of said characteristic in the total thoroughbred racehorse population;
the improvement comprising:
   b. means for creating said profile and dividing said profile into increments of measurements and identifying the increments;
   c. means for determining a measurement of said representative physical characteristic in the form of a combined body length (CBL) in a given racehorse and its ancestors;
   d. means for creating a genetic dominance tree (GDT) of the given racehorse and its ancestors;
   e. means for identifying in said genetic dominance tree (GDT) of the given horse the increment of the representative physical characteristic in the form of a combined body length (CBL) of said profile in which the measurement of the representative physical characteristics of the given racehorse and each of its ancestors, where known, falls;
   f. and means for determining any dominant and substantially constant increment of the representative physical characteristic in the form of a combined body length (CBL) of the profile of the total thoroughbred racehorse population that exists in the genetic dominance tree (GDT) of the given racehorse;
wherein the genetic dominance tree (GDT) of both the sire and the dam selected for breeding have the same dominant and substantially constant increment of the representative physical characteristic in the form of a combined body length (CBL).

2. The system of claim 1 wherein the combined body length (CBL) is the sum of the distances A and B measured on a horse in a relaxed, standing position where A is the distance from the rear corner of the racehorse's eye to a middle point on the front of the horse's scapula, and B is a the distance from the same point on the racehorse's scapula to the hind point on the skin over the horse's ischium.

3. The system of claim 1 wherein the means for creating said profile and dividing said profile into increments and identifying the increments, is a chart.

4. The system of claim 3 wherein the means for identifying the increments in the profile and the genetic dominance tree (GDT) is color.

5. The system of claim 3 wherein the means for identifying the increment in the profile and the genetic dominance tree (GDT) is a number.

6. The system of claim 2 wherein the combined body length (CBL) in the profile is in a range between 85 inches and 96 inches.

7. The system of claim 6 wherein the profile is divided into 1 inch increments.

8. The system of claim 7 wherein the means for creating said profile and dividing said profile into increments is in chart form.

9. The system of claim 8, wherein the increments are represented in the chart by bars.

10. The system of claim 9 wherein the chart is a Bell curve.

11. The system of claim 4 wherein the dominant increment of the representative physical characteristic in the form of a combined body length (CBL) if any, in the genetic dominance tree (GDT), is identified by the predominance of the same color on the given racehorse and its ancestors.

12. The system of claim 1 wherein the genetic dominance tree (GDT) includes the progeny of the given horse and its ancestors.

13. In a method of selecting a sire and a dam for breeding a racehorse:
   a. determining a measurement of a representative physical characteristic in the form of a combined body length (CBL) on each of a sufficient number of thoroughbred racehorses to yield a representative profile of the measurements of said characteristic in the total thoroughbred racehorse population;
the improvement comprising:
   b. creating said profile and dividing said profile into increments of measurements and identifying the increments;
   c. determining a measurement of said representative physical characteristic in the form of a combined body length (CBL) in a given racehorse and its ancestors;
   d. creating a genetic dominance tree (GDT) of the given racehorse and its ancestors;
   e. identifying in said genetic dominance tree (GDT) of the given horse the increment of the representative physical characteristic in the form of a combined body length (CBL) of said profile in which the measurement of the representative physical characteristics of the given racehorse and each of its ancestors, where known, falls;
   f. determining any dominant and substantially constant increment of the representative physical characteristic in the form of a combined body length (CBL) of the profile of the total thoroughbred racehorse population that exists in the genetic dominance tree (GDT) of the given racehorse; and
   g. selecting a sire and dam for breeding wherein the genetic dominance tree (GDT) of both the sire and the dam selected for breeding have the same dominant and substantially constant increment of the representative physical characteristic in the form of a combined body length (CBL).

14. The method of claim 13 wherein the combined body length (CBL) is the sum of the distances A and B measured on a horse in a relaxed, standing position where A is the distance from the rear corner of the racehorse's eye to a middle point on the front of the horse's scapula, and B is a the distance from the same point on the racehorse's scapula to the hind point on the skin over the horse's ischium.

15. The method of claim 13 wherein creating said profile and dividing said profile into increments and identifying the increment, is done with a chart.

16. The method of claim 15 wherein identifying the increments in the profile and in the genetic dominance tree (GDT) is done with color.

17. The method of claim 15 wherein identifying the increment in the profile and the genetic dominance tree (GDT) is done with a number.

18. The method of claim 14 wherein the combined body length (CBL) in the profile is in a range between 85 inches and 96 inches.

19. The method of claim 18 wherein the profile is divided into 1 inch increments.

20. The method of claim 19 wherein creating said profile and dividing said profile into the increments is done in chart form.

21. The method of claim 20, wherein the increments are represented in the chart by bars.

22. The method of claim 21 wherein the chart is a Bell curve.

23. The method of claim 16 wherein the dominant increment of the representative physical characteristic in the form of a combined body length (CBL) if any, in the genetic dominance tree (GDT), is identified by the predominance of the same color on the given racehorse and its ancestors.

24. The method of claim 13 wherein the genetic dominance tree (GDT) includes the progeny of the given horse and its ancestors.

* * * * *